(12) United States Patent
Wu (10) Patent No.: US 9,068,911 B2
(45) Date of Patent: Jun. 30, 2015

(54) MULTIFUNCTION GAUGE

(71) Applicant: KMC CHAIN INDUSTRIAL CO., LTD., Tainan (TW)

(72) Inventor: Daniel Wu, Tainan (TW)

(73) Assignee: KMC Chain Industrial Co., Ltd., Tainan (TW)

( * ) Notice: Subject to any disclaimer, the term of this patent is extended or adjusted under 35 U.S.C. 154(b) by 0 days.

(21) Appl. No.: 14/138,332

(22) Filed: Dec. 23, 2013

(65) Prior Publication Data

US 2014/0174194 A1 Jun. 26, 2014

(30) Foreign Application Priority Data

Dec. 26, 2012 (TW) .............................. 101150152 A (51) Int. Cl.

| | |
|---|---|
| *F16G 13/00* | (2006.01) |
| *G01B 5/16* | (2006.01) |
| *G01B 5/14* | (2006.01) |
| *G01N 3/56* | (2006.01) |
| *G01N 3/16* | (2006.01) |
| *B25B 27/00* | (2006.01) |
| *B25B 27/22* | (2006.01) |

(52) U.S. Cl.
CPC .. *G01N 3/56* (2013.01); *G01N 3/16* (2013.01); *B25B 27/0071* (2013.01); *B25B 27/22* (2013.01)

(58) Field of Classification Search
CPC ............. F16G 13/00; G01B 5/14; G01B 5/16
USPC ........................................................... 73/828
See application file for complete search history.

(56) References Cited

U.S. PATENT DOCUMENTS

| | | | | |
|---|---|---|---|---|
| 5,348,515 | A * | 9/1994 | Miller ........................... | 474/152 |
| 6,178,824 | B1 * | 1/2001 | Hayakawa et al. ............. | 73/828 |
| 7,018,313 | B2 * | 3/2006 | Nakamura ..................... | 474/152 |
| 7,654,149 | B2 * | 2/2010 | Wilbur ............................ | 73/829 |
| 2004/0002402 | A1 * | 1/2004 | Nakamura ..................... | 474/156 |
| 2009/0193907 | A1 * | 8/2009 | Wilbur ............................ | 73/829 |

OTHER PUBLICATIONS

Rohloff GmbH, Rohloee HG-IG-Check user manual, Rohloff GmbH, http://www.rohloff.de/uploads/media/Beschreibung_HG_IG_Check.en.pdf, Nov. 11, 2000.
Search Report and English translation in Taiwanese Application Serial No. 101150152 issued Jul. 14, 2014.

\* cited by examiner

*Primary Examiner* — Lisa Caputo
*Assistant Examiner* — Jamel Williams
(74) *Attorney, Agent, or Firm* — Nixon & Vanderhye P.C.

(57) ABSTRACT

A multifunction gauge includes a checking bar adapted to check wear of a roller chain, and a flexible checking member adapted to check wear of a sprocket and connected to the checking bar. The checking bar has a bar body that has opposite first and second end portions respectively having opposite first and second terminating ends. The checking bar further has spaced-apart first and second checking projections that project transversely from one side of the bar body.

11 Claims, 11 Drawing Sheets

MULTIFUNCTION GAUGE

CROSS-REFERENCE TO RELATED APPLICATION

This application claims priority of Taiwanese Application No. 101150152, filed on Dec. 26, 2012.

BACKGROUND OF THE INVENTION

1. Field of the Invention

The invention relates to a multifunction gauge, more particularly to a multifunction gauge for checking wear of a sprocket and a roller chain.

2. Description of the Related Art

The sprockets and the roller chain of a drivetrain system for a bicycle may be worn after long-term use. A worn roller chain is lengthened, and may easily derail from the sprockets when being used in a single-speed bicycle, or affect the function of a rear derailleur when being used in a variable-ratio transmission system of a different kind of bicycle. A worn sprocket may easily slip relative to a roller chain and may not drive or be driven by the roller chain properly. Therefore, the sprockets and the roller chain of a bicycle need to be checked periodically.

There are separate sprocket and chain wear gauges for checking sprocket wear and roller chain wear, respectively. However, to check wearing of the drivetrain system of a bicycle, both of the sprocket wear gauge and the chain wear gauge are needed.

SUMMARY OF THE INVENTION

Therefore, the object of the present invention is to provide a multifunction gauge for checking wear of both a sprocket and a roller chain.

Accordingly, a multifunction gauge of the present invention is adapted for checking wear of a sprocket and a roller chain. The sprocket has a plurality of angularly spaced-apart sprocket teeth, and a plurality of sprocket grooves each being defined between a corresponding adjacent pair of the sprocket teeth. The roller chain includes a plurality of spaced-apart rollers, and a plurality of chain grooves each being defined between a corresponding adjacent pair of the rollers. The multifunction gauge includes a checking bar adapted to check wear of the roller chain, and a flexible checking member adapted to check wear of the sprocket and connected pivotally to the checking bar. The checking bar has a bar body that has opposite first and second end portions. The first end portion has a first terminating end adapted to engage one of the sprocket grooves when the flexible checking member is used to check wear of the sprocket. The second end portion is formed into a rod-shaped handle adapted for applying force when the flexible checking member is used to check wear of the sprocket. The second end portion has a second terminating end that is opposite to the first terminating end along a longitudinal direction of the checking bar. The checking bar further has spaced-apart first and second checking projections that project transversely from one side of the bar body between the first and second terminating ends and that are adapted to check wear of the roller chain. The first checking projection is proximal to the first terminating end. The second checking projection is proximal to the second terminating end of the second end portion.

BRIEF DESCRIPTION OF THE DRAWINGS

Other features and advantages of the present invention will become apparent in the following detailed description of the preferred embodiments with reference to the accompanying drawings, of which.

DETAILED DESCRIPTION OF THE PREFERRED EMBODIMENTS

Before the present invention is described in greater detail, it should be noted that like elements are denoted by the same reference numerals throughout the disclosure.

Figure 1:
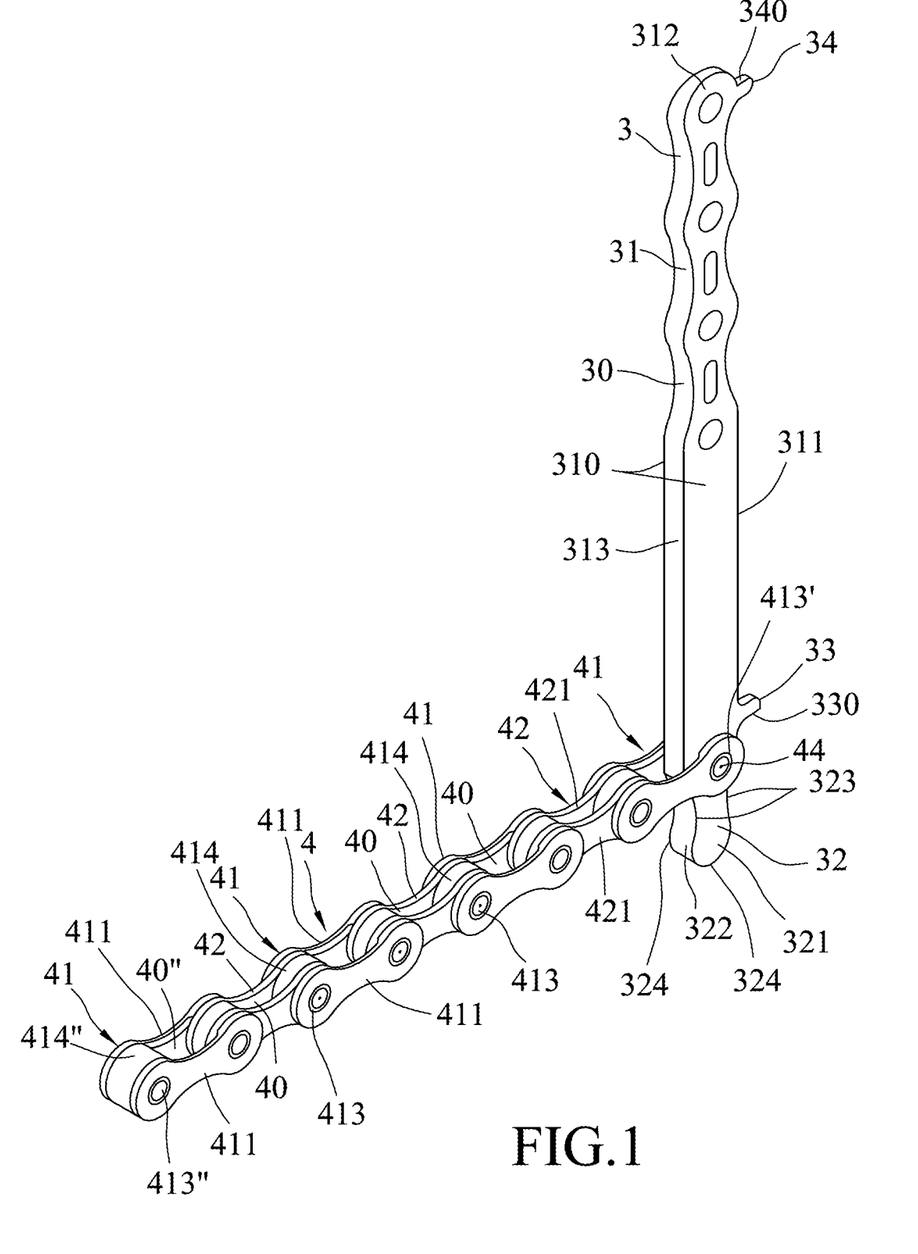
FIG. 1 is a perspective view of a first preferred embodiment of a multifunction gauge according to the invention.
Figure 2:
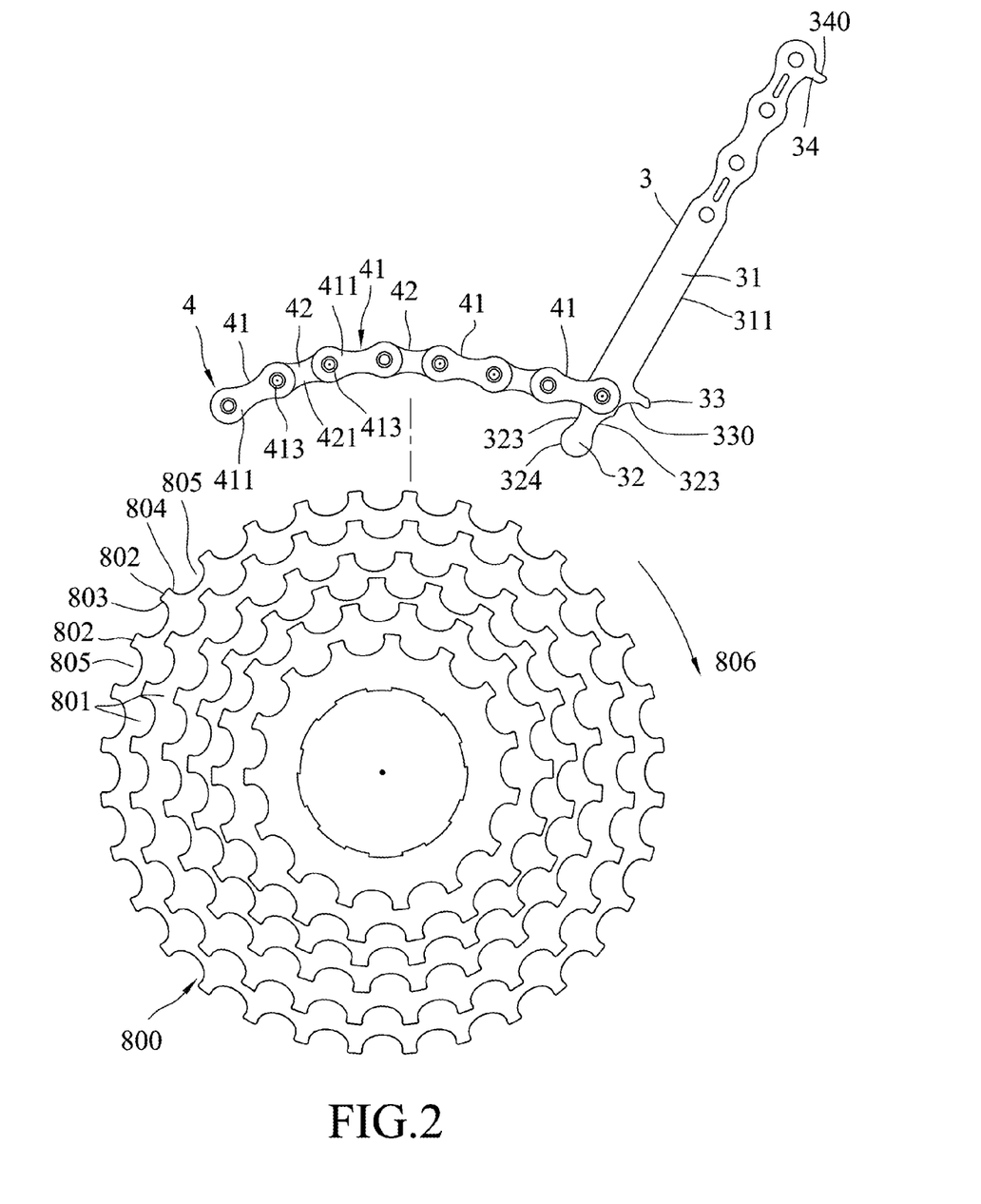
FIG. 2 is a side view of the first preferred embodiment and a sprocket assembly.
Figure 6:
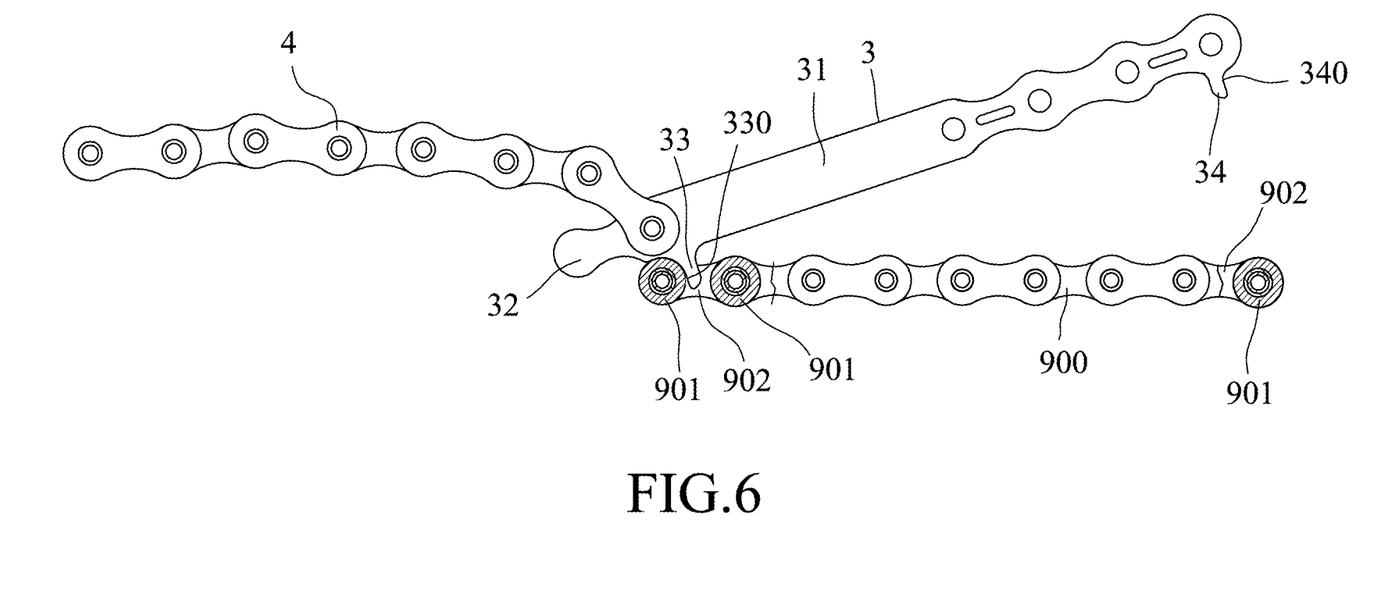
FIG. 6 is a schematic side view illustrating the first preferred embodiment in a used state for checking wear of a roller chain.

As shown in FIG. 1, the first preferred embodiment of a multifunction gauge according to the present invention is adapted for checking wear of a drivechain of a bicycle (not shown) which includes a roller chain 900 (see FIG. 6) and a cogset 800 (a sprocket assembly, see FIG. 2). Referring to FIG. 2, the cogset 800 includes a plurality of sprockets 801 each having a plurality of angularly spaced-apart sprocket teeth 802, and a plurality of sprocket grooves 805. Each of the sprocket grooves 805 is defined between a corresponding adjacent pair of the sprocket teeth 802. Each of the sprocket teeth 802 has a first abutment surface 803 and a second abutment surface 804 opposite to the first abutment surface 803. Generally, the cogset 800 is driven by a roller chain (not shown) to rotate in a rotational direction 806, so the first abutment surface 803 of each of the sprocket teeth 802 is worn more seriously than the second abutment surface 804. Referring to FIG. 6, the roller chain 900 includes a plurality of spaced-apart rollers 901, and a plurality of chain grooves 902, each of which is defined between a corresponding adjacent pair of the rollers 901.

Figure 5:
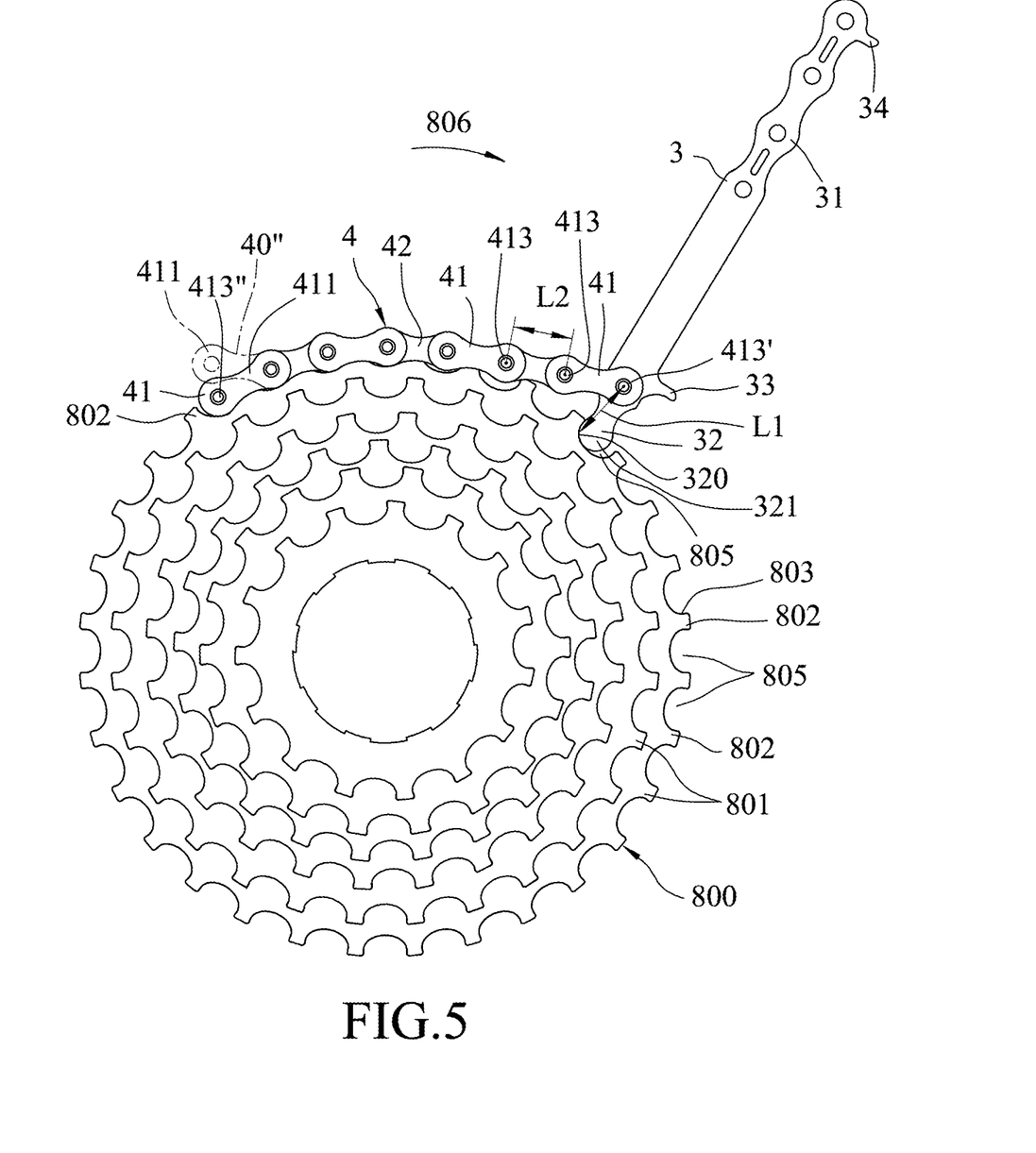
FIG. 5 is the same view as FIG. 3 but illustrating that the first preferred embodiment is operated under a different mode for checking wear of the sprocket assembly.

Referring to FIGS. 1, 5 and 6, the multifunction gauge includes a checking bar 3 adapted to check wear of the roller chain 900, and a flexible checking member 4 adapted to check wear of the sprockets 801 and connected pivotally to the checking bar 3.

The checking bar 3 has a bar body 30 and spaced-apart first and second checking projections 33, 34.

The bar body 30 is configured as a flat bar, and has two opposite planar side surfaces 310 facing oppositely away from each other, a rule surface 311 interconnecting the side surfaces 310, and opposite first and second end portions 32, 31.

The first end portion 32 has a first terminating end 321 adapted to engage one of the sprocket grooves 805 when the flexible checking member 4 is used to check wear of the sprocket 801. Each of the side surfaces 310 has a rounded periphery 324 at the first terminating end 321. The first end portion 32 further has a rounded end surface 322 that is disposed transversely between the side surfaces 310 and that interconnects the rounded peripheries 324 of the side surfaces 310. The rounded end surface 322 has a contact point 320 (see FIG. 5) for contacting the sprocket 801 when the flexible checking member 4 is used to check the wear of the sprocket 801. The first end portion 32 further has two concaved surfaces 323 that are connected respectively to opposite ends of the rounded end surface 322. Each of the concaved surfaces 323 interconnects the side surfaces 310.

The second end portion 31 is formed into a rod-shaped handle adapted for applying force when the flexible checking member 4 is used to check wear of the sprocket 801. The second end portion 31 has a second terminating end 312 that is opposite to the first terminating end 321 along a longitudinal direction of the bar body 30.

The first and second checking projections 33, 34 project from the rule surface 311 of the bar body 30 transversely of the longitudinal direction between the first and second terminating ends 321, 312 and are adapted to check wear of the roller chain 900. The first checking projection 33 is proximal to the first terminating end 321. The second checking projection 34 is proximal to the second terminating end 312.

The first checking projection 33 has a first abutment surface 330 that faces oppositely away from the second checking projection 34. The second checking projection has a second abutment surface 340 that faces oppositely away from the first checking projection 33 and that is flat. In this embodiment, the first abutment surface 330 has a curved or concave profile, but can also be flat.

A thickness of the bar body 30 decreases toward the rule surface 311 from a back surface 313. Each of the first and second checking projections 33, 34 has a thickness that decreases from the rule surface 311 in a direction away from the rule surface 311.

The flexible checking member 4 is pivoted to the first end portion 32 of the bar body 30 of the checking bar 3 at a pivot point 44 between the first terminating end 321 and the first checking projection 33. The structure and specification of the flexible checking member 4 is substantially the same as that of the roller chain 900.

The flexible checking member 4 includes a plurality of first and second link units 41, 42 that are interconnected in series in alternating arrangement. Each of the first and second link units 41, 42 has two link plates 411, 421. The number of the first and second link units 41, 42 of the flexible checking member 4 depends on the number of the sprocket teeth 802 of the sprocket 801. In this embodiment, the flexible checking member 4 includes four first link units 41 and three second link units 42. The flexible checking member 4 further includes a plurality of connecting pins 413, each of which interconnects pivotally a corresponding adjacent pair of the first and second link units 41, 42, a proximal pin 413' that is disposed at the pivot point 44 and that interconnects pivotally a proximal end portion of a proximal one of the first and second link units 41, 42 (i.e., the first link unit 41 that is proximal to the checking bar 3 in FIG. 1) and the first end portion 32 of the checking bar 3, a distal pin 413" that is inserted in a distal end portion of a distal one of the first and second link units 41, 42 (i.e., the first link unit 41 that is distal from the checking bar 3 in FIG. 1), a plurality of rollers 414 that surround rotatably and respectively the connecting pins 413, a distal roller 414" that surrounds fittingly the distal pin 413", a plurality of sprocket tooth engaging spaces 40, each of which is defined between a corresponding adjacent pair of the rollers 414, and a distal sprocket tooth engaging space 40" that is define between the distal roller 414" and one of the rollers 414 adjacent to the distal roller 414". Preferably, the number of the sprocket tooth engaging spaces 40 ranges from 2 to 14. The proximal pin 413' extends through the side surfaces 310 of the bar body 30 such that the side surfaces 310 are opposite to each other in an axial direction of the proximal pin 413'. The distal roller 414" is clamped between the link plates 411 of the distal one of the first link units 41 and is non-rotatable relative to the link plates 411 of the distal one of the first link units 41. The distal roller 414" is greater than the rollers 414 in thickness. Referring to FIG. 5, in this embodiment, a distance between the proximal pin 413' and the contact point 320 is not smaller than a distance between an adjacent pair of the connecting pins 413.

Figure 3:
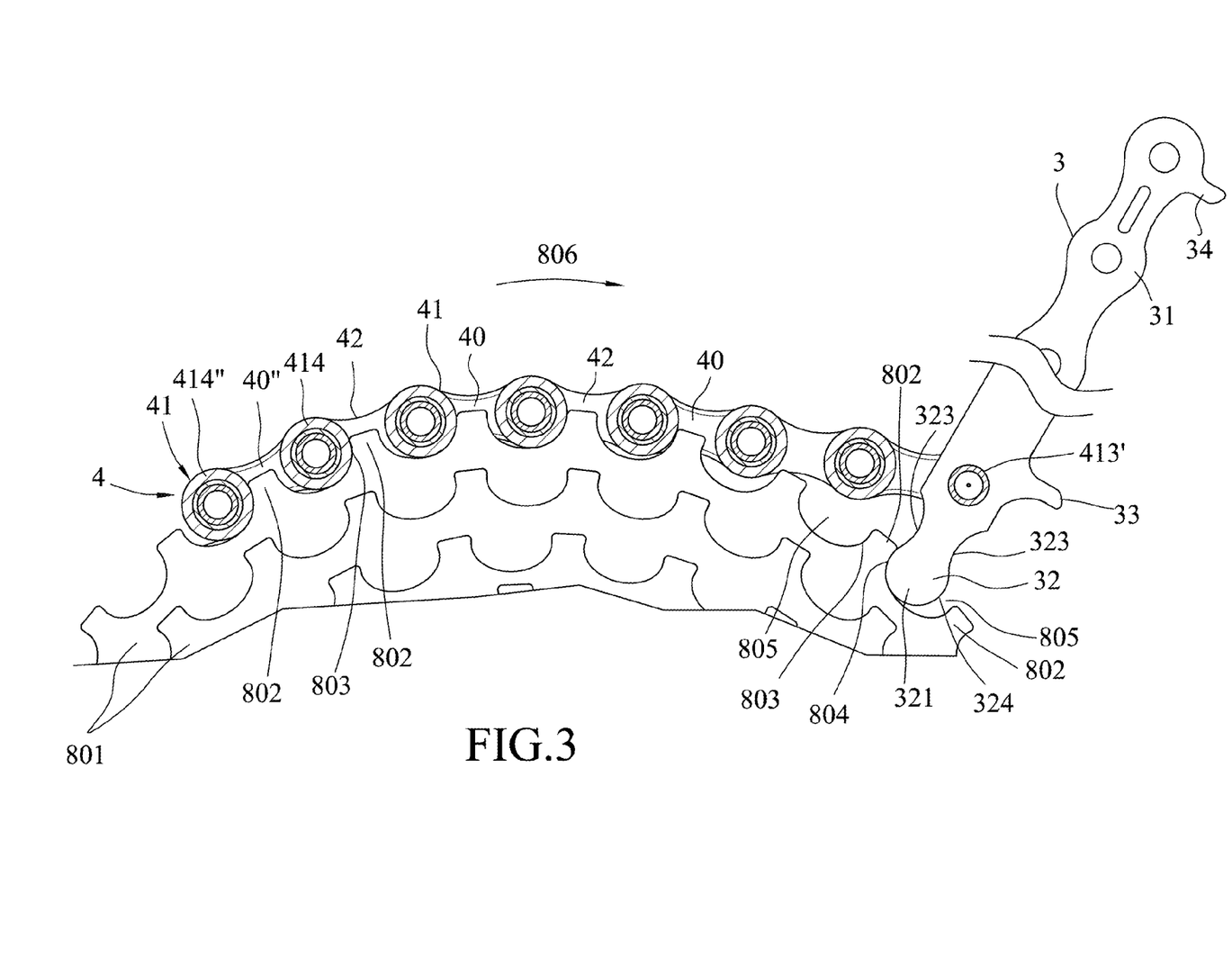
FIG. 3 is a fragmentary schematic side view illustrating the first preferred embodiment in a used state in which wear of the sprocket assembly is checked.
Figure 4:
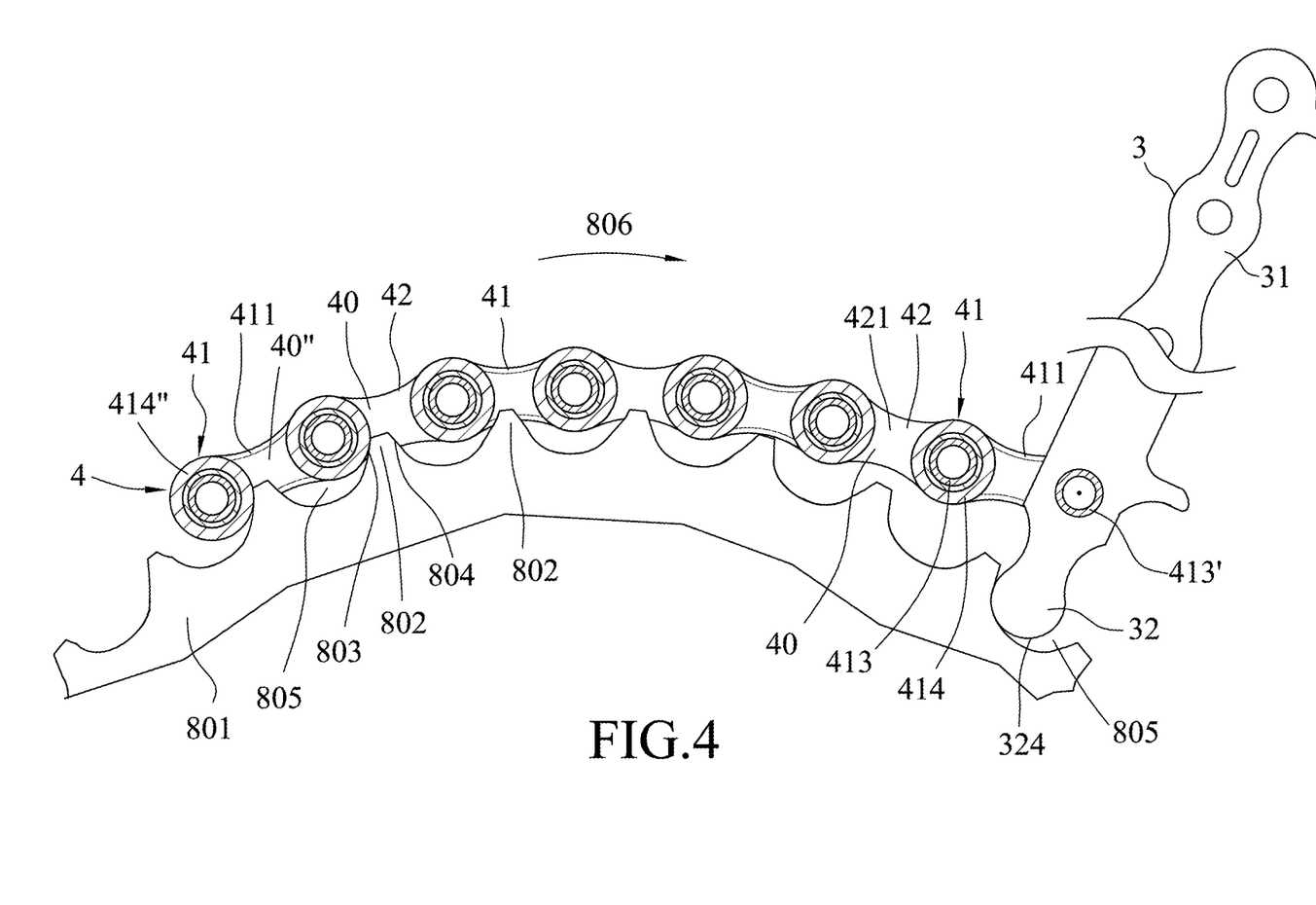
FIG. 4 is the same view as FIG. 3 but illustrating that the sprocket assembly is worn.

Referring to FIGS. 3 and 4, when the first preferred embodiment of the multifunction gauge is used to check wear of a sprocket 801, the sprocket tooth engaging spaces 40 and the distal sprocket tooth engaging space 40" of the flexible checking member 4 are engaged respectively with a plurality of successive sprocket teeth 802 of the sprocket 801, and the first terminating end 321 of the first end portion 32 of the checking bar 3 engages one of the sprocket grooves 805 of the sprocket 801. A force is applied to the checking bar 3 in the rotational direction 806 such that the flexible checking member 4 is tensed. If the sprocket 801 is in a normal condition (see FIG. 3), the flexible checking member 4 may be retained stably on the sprocket teeth 802 and will not disengage from the sprocket 801. If the sprocket 801 is worn seriously (see FIG. 4), the flexible checking member 4 may slip from the sprocket teeth 802 and move in the rotational direction 806 by the force. While the concaved surfaces 323 of the first end portion 32 are provided in this embodiment, they are not indispensable. The presence of the concaved surfaces 323 is for avoiding the interference between the first end portion 32 and the sprocket teeth 802 when the multifunction gauge is used to check the wear of the sprocket 801.

Referring to FIG. 5, in an alternative approach, wear of the sprocket 801 is checked by the multifunction gauge when the first abutment surface 803 of each of the sprocket teeth 802 is worn slightly. Firstly, the sprocket tooth engaging spaces 40 (see FIG. 1) are engaged respectively with a plurality of successive sprocket teeth 802 of the sprocket 801, and the first terminating end 321 of the first end portion 32 of the checking bar 3 engages one of the sprocket grooves 805 of the sprocket 801. However, the distal one of the first link units 41 is placed away from the sprocket 801 (as shown in dashed lines). Thereafter, a force is applied to the checking bar 3 in the rotational direction 806 such that the flexible checking member 4 is tensed, and the distal one of the first link units 41 is simultaneously caused to move toward the corresponding sprocket tooth 802. If the sprocket 801 is worn slightly, the corresponding sprocket tooth 802 is unable to enter smoothly the distal sprocket tooth engaging space 40".

It is noted that when the sprocket teeth 802 of the sprocket 801 are worn slightly, the second approach is efficient to obtain more accurate results.

Figure 7:
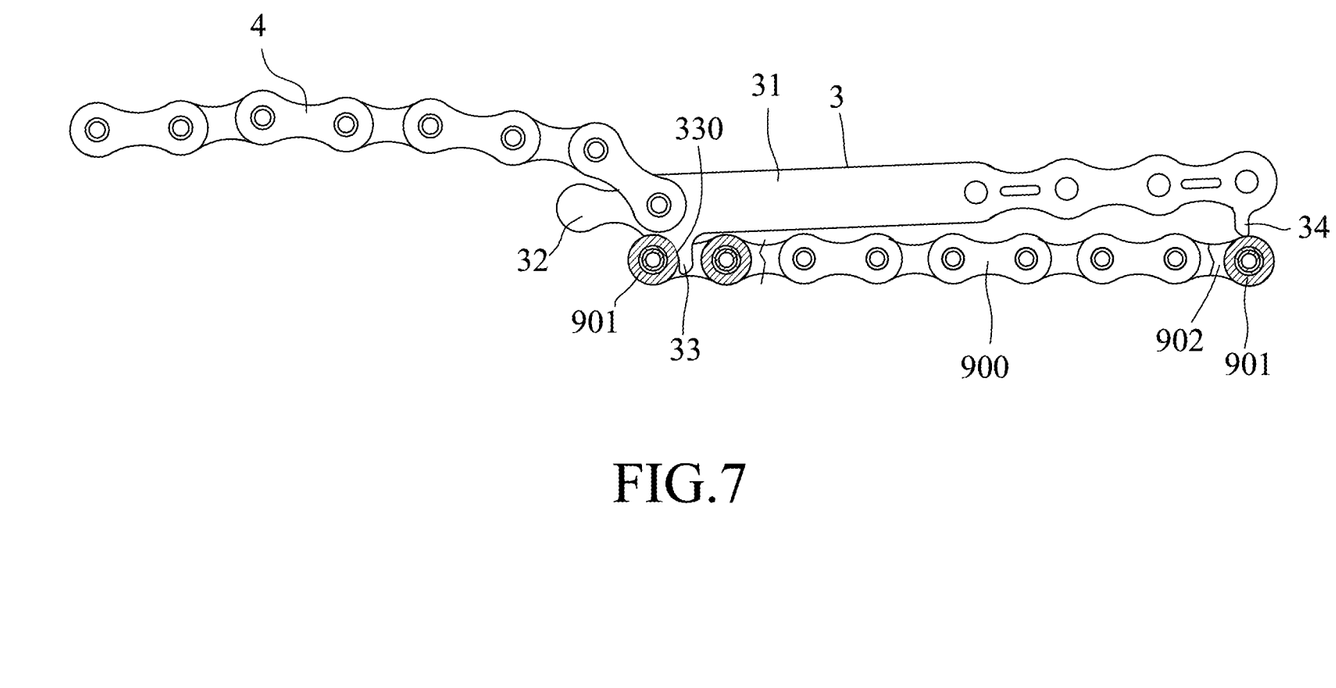
FIG. 7 is the same view as FIG. 6 but indicating that the roller chain is in a normal condition.
Figure 8:
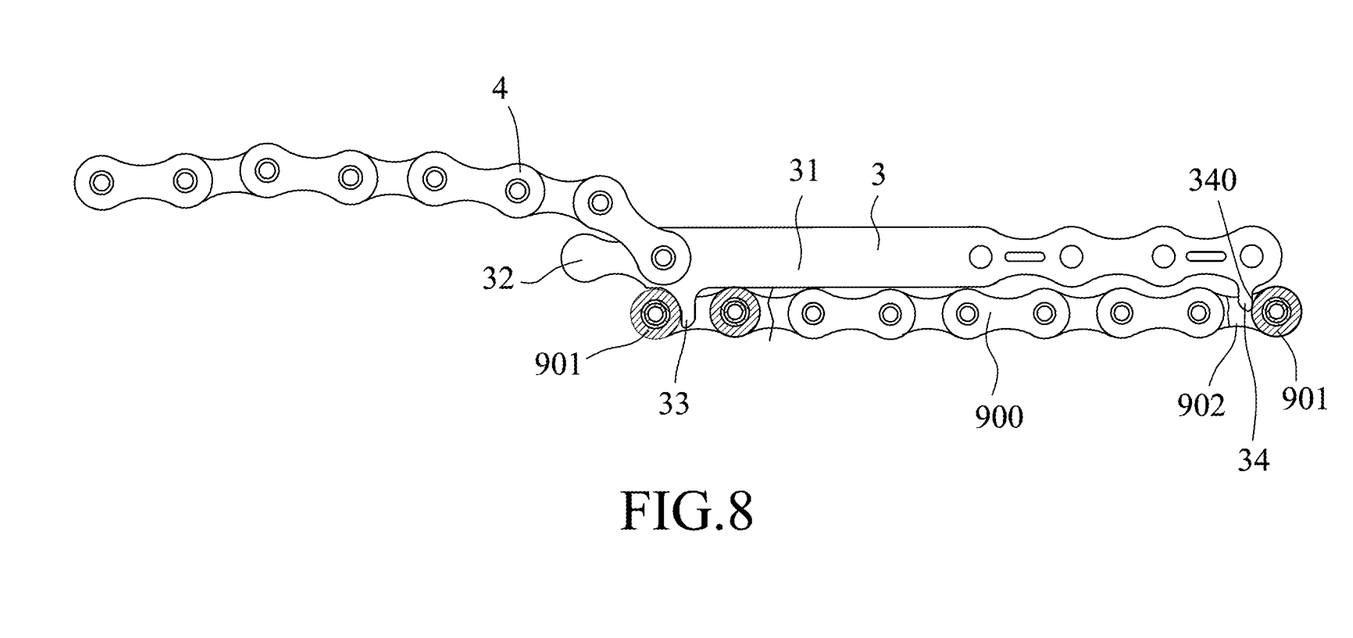
FIG. 8 is the same view as FIG. 6 but indicating that the roller chain is worn seriously.

Referring to FIG. 6, when the first preferred embodiment of the multifunction gauge is used to check wear of the roller chain 900, the first checking projection 33 is first inserted into one of the chain grooves 902 with the first abutment surface 330 abutting against a corresponding first roller 901, and then the checking bar 3 is moved toward the roller chain 900 to check if the second checking projection 34 can be inserted into a predetermined chain groove 902. In this embodiment, the predetermined chain groove 902 is the eighth chain groove 902 counted from the corresponding first roller 901. If the second checking projection 34 cannot be inserted into the predetermined chain groove 902 (see FIG. 7), the roller chain 900 is in a normal condition. If the second checking projection 34 can be inserted into the predetermined chain groove 902 (see FIG. 8), the roller chain 900 may need to be replaced since it has been lengthened due to wear.

To sum up, the multifunction gauge of this invention is capable of checking wear of the roller chain 900 and the sprockets 801 of the drivechain of the bicycle. Compared with conventional separate chain and sprocket wear gauges, the multifunction gauge is more convenient.

Figure 9:
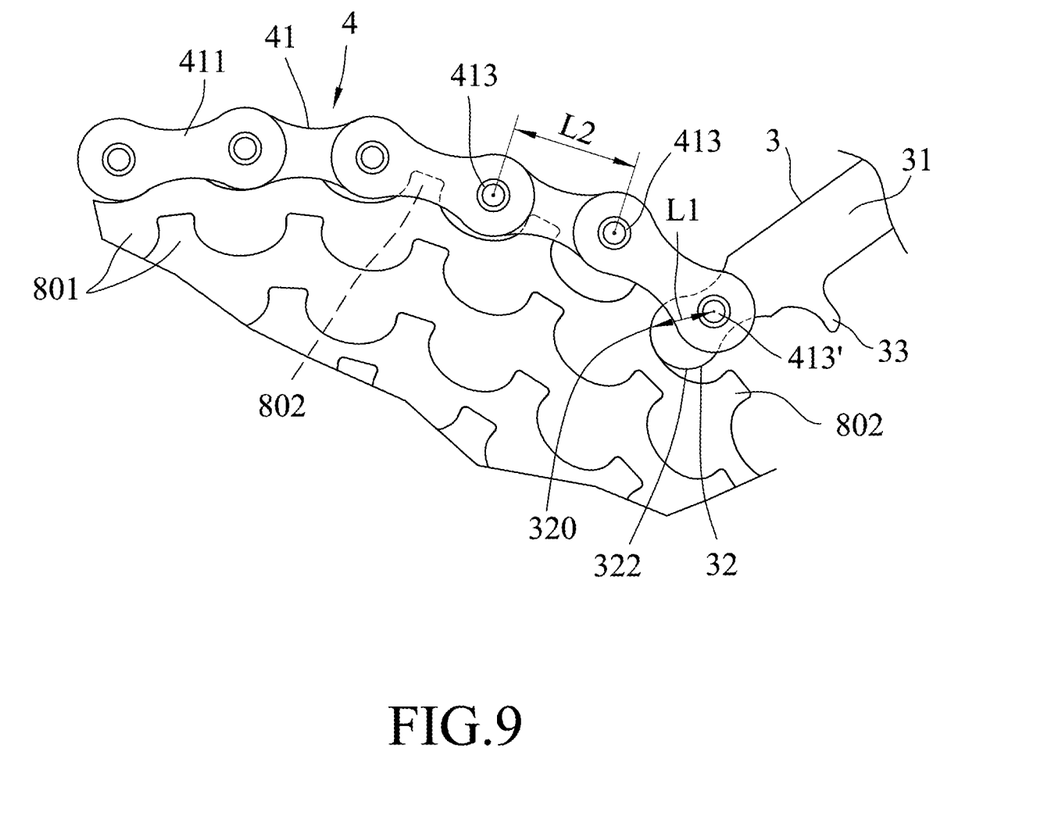
FIG. 9 is a fragmentary side view of a second preferred embodiment of a multifunction gauge according to the invention.

Referring to FIG. 9, a second preferred embodiment of the multifunction gauge according to the present invention is generally similar to the first preferred embodiment in structure. The difference between the first and second preferred embodiments resides in that a distance (L1) between the proximal pin 413' and the contact point 320 of the second preferred embodiment is not smaller than a half of a distance (L2) between an adjacent pair of the connecting pins 413.

Figure 10:
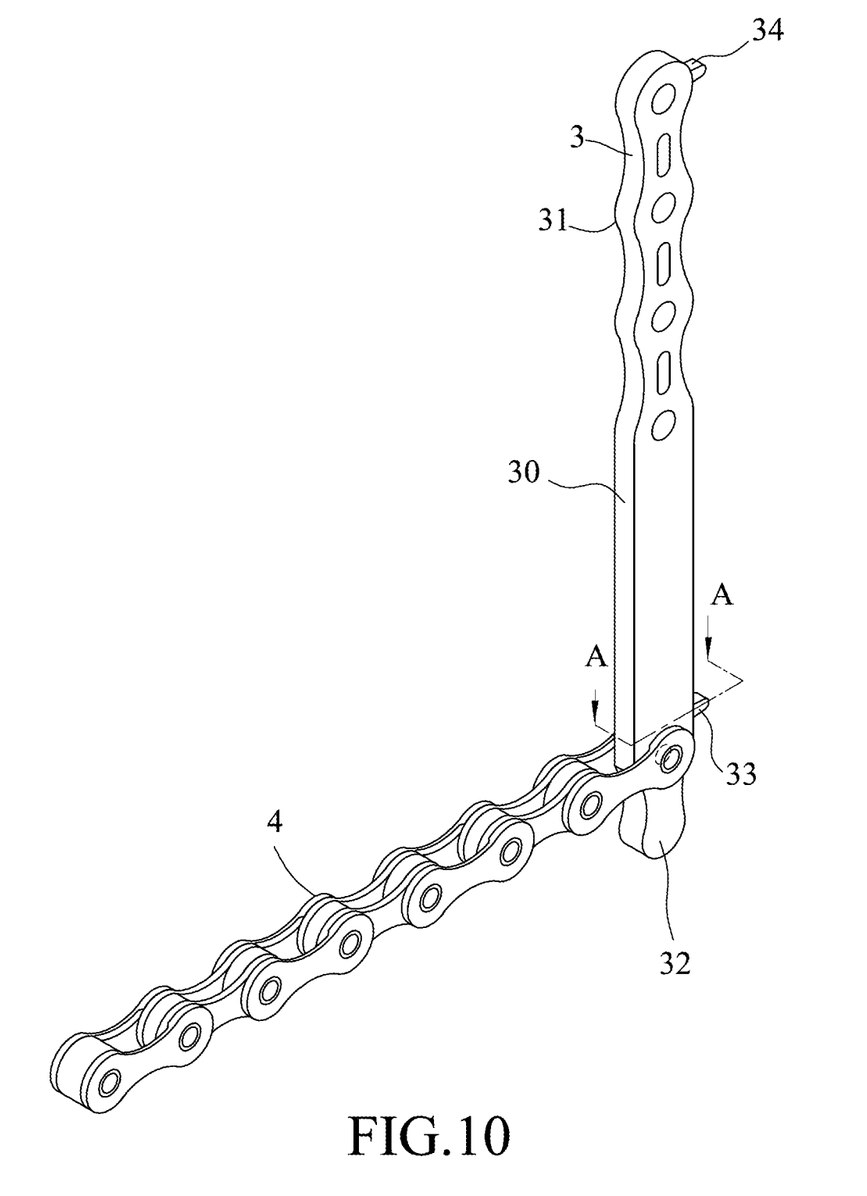
FIG. 10 is a perspective view of a third preferred embodiment of a multifunction gauge according to the invention.
Figure 11:
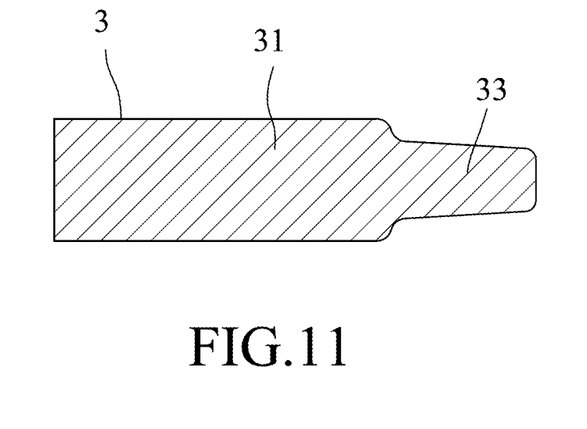
FIG. 11 is a sectional view of the third preferred embodiment taken along line A-A in FIG. 10.

Referring to FIGS. 10 and 11, a third preferred embodiment of the multifunction gauge according to the present invention is different from the first preferred embodiment in that the bar body 30 has a uniform thickness, and that the bar body 30 is greater than the first and second checking projections 33, 34 in thickness.

While the present invention has been described in connection with what are considered the most practical and preferred embodiments, it is understood that this invention is not limited to the disclosed embodiments but is intended to cover various arrangements included within the spirit and scope of the broadest interpretation so as to encompass all such modifications and equivalent arrangements.

What is claimed is:

1. A multifunction gauge for checking wear of a sprocket and a roller chain, the sprocket having a plurality of angularly spaced-apart sprocket teeth, and a plurality of sprocket grooves each being defined between a corresponding adjacent pair of the sprocket teeth, the roller chain including a plurality of spaced-apart rollers, and a plurality of chain grooves each being defined between a corresponding adjacent pair of the rollers, said multifunction gauge comprising:
   a checking bar adapted to check wear of the roller chain, and a flexible checking member adapted to check wear of the sprocket and connected pivotally to said checking bar;
   said checking bar having a bar body that has opposite first and second end portions, said first end portion having a first terminating end adapted to engage one of the sprocket grooves when said flexible checking member is used to check wear of the sprocket, said second end portion being formed into a rod-shaped handle adapted for applying force when said flexible checking member is used to check wear of the sprocket, said second end portion having a second terminating end that is opposite to said first terminating end along a longitudinal direction of said bar body;
   said checking bar further having spaced-apart first and second checking projections that project transversely from said bar body between said first and second terminating ends and that are adapted to check wear of the roller chain, said first checking projection being proximal to said first terminating end, said second checking projection being proximal to said second terminating end of said second end portion;
   wherein said first checking projection has a first abutment surface that faces oppositely away from said second checking projection and that has a curved profile, said second checking projection having a second abutment surface that faces oppositely away from said first checking projection; and
   wherein said flexible checking member includes
      a plurality of link units that are interconnected in series,
      a plurality of connecting pins, each of which interconnects pivotally a corresponding adjacent pair of said link units,
      a proximal pin that is disposed at a pivot point and that interconnects pivotally a proximal end portion of a proximal one of said link units and said first end portion of said bar body,
      a distal pin that is inserted in a distal end portion of a distal one of said link units,
      a plurality of rollers that surround rotatably and respectively said connecting pins,
      a distal roller that surrounds said distal pin,
      a plurality of sprocket tooth engaging spaces, each of which is defined between a corresponding adjacent pair of said rollers, and
      a distal sprocket tooth engaging space that is define between said distal roller and one of said rollers adjacent to said distal roller.

2. The multifunction gauge as claimed in claim 1, wherein a number of said sprocket tooth engaging spaces ranges from 2 to 14.

3. The multifunction gauge as claimed in claim 1, wherein said bar body of said checking bar has
   two opposite planar side surfaces which face oppositely away from each other in an axial direction of said proximal pin and each of which has a rounded periphery at said first terminating end, and
   a rounded end surface that is disposed transversely between said side surfaces and that interconnects said rounded peripheries of said side surfaces, said rounded end surface having a contact point for contacting the sprocket when said flexible checking member is used to check the wear of the sprocket.

4. The multifunction gauge as claimed in claim 3, wherein said first end portion further has at least one concaved surface that is connected to one end of said rounded end surface and that interconnects said side surfaces.

5. The multifunction gauge as claimed in claim 3, wherein a distance between said proximal pin and said contact point is not smaller than half of a distance between an adjacent pair of said connecting pins.

6. The multifunction gauge as claimed in claim 3, wherein a distance between said proximal pin and said contact point is not smaller than a distance between an adjacent pair of said connecting pins.

7. The multifunction gauge as claimed in claim 3, wherein said distal roller is greater than said rollers in thickness.

8. The multifunction gauge as claimed in claim 1, wherein said distal roller is non-rotatable.

9. The multifunction gauge as claimed in claim 1, wherein said bar body of said checking bar is configured as a flat bar, and has
   two planar side surfaces facing oppositely away from each other, a rule surface interconnecting said side surfaces and connected to said first and second projections, and a back surface opposite to said rule surface, a thickness of said bar body decreasing toward said rule surface from said back surface.

10. A multifunction gauge for checking wear of a sprocket and a roller chain, the sprocket having a plurality of angularly spaced-apart sprocket teeth, and a plurality of sprocket grooves each being defined between a corresponding adjacent pair of the sprocket teeth, the roller chain including a plurality of spaced-apart rollers, and a plurality of chain grooves each being defined between a corresponding adjacent pair of the rollers, said multifunction gauge comprising:

a checking bar adapted to check wear of the roller chain, and a flexible checking member adapted to check wear of the sprocket and connected pivotally to said checking bar;

said checking bar having a bar body that has opposite first and second end portions, said first end portion having a first terminating end adapted to engage one of the sprocket grooves when said flexible checking member is used to check wear of the sprocket, said second end portion being formed into a rod-shaped handle adapted for applying force when said flexible checking member is used to check wear of the sprocket, said second end portion having a second terminating end that is opposite to said first terminating end along a longitudinal direction of said bar body;

said checking bar further having spaced-apart first and second checking projections that project transversely from said bar body between said first and second terminating ends and that are adapted to check wear of the roller chain, said first checking projection being proximal to said first terminating end, said second checking projection being proximal to said second terminating end of said second end portion;

wherein said bar body is greater than said first and second checking projections in thickness.

11. A multifunction gauge for checking wear of a sprocket and a roller chain, the sprocket having a plurality of angularly spaced-apart sprocket teeth, and a plurality of sprocket grooves each being defined between a corresponding adjacent pair of the sprocket teeth, the roller chain including a plurality of spaced-apart rollers, and a plurality of chain grooves each being defined between a corresponding adjacent pair of the rollers, said multifunction gauge comprising:

a checking bar adapted to check wear of the roller chain, and a flexible checking member adapted to check wear of the sprocket and connected pivotally to said checking bar;

said checking bar having a bar body that has opposite first and second end portions, said first end portion having a first terminating end adapted to engage one of the sprocket grooves when said flexible checking member is used to check wear of the sprocket, said second end portion being formed into a rod-shaped handle adapted for applying force when said flexible checking member is used to check wear of the sprocket, said second end portion having a second terminating end that is opposite to said first terminating end along a longitudinal direction of said bar body;

said checking bar further having spaced-apart first and second checking projections that project transversely from said bar body between said first and second terminating ends and that are adapted to check wear of the roller chain, said first checking projection being proximal to said first terminating end, said second checking projection being proximal to said second terminating end of said second end portion;

wherein said flexible checking member is pivoted to said first end portion of said checking bar at a pivot point between said first terminating end and said first checking projection.

* * * * *